(12) United States Patent
Srinivasan

(10) Patent No.: US 8,098,910 B2
(45) Date of Patent: Jan. 17, 2012

(54) ADAPTIVE MOTION IMAGING IN MEDICAL DIAGNOSTIC ULTRASOUND IMAGING

(75) Inventor: Seshadri Srinivasan, Mountain View, CA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 1162 days.

(21) Appl. No.: 11/900,624

(22) Filed: Sep. 11, 2007

(65) Prior Publication Data
US 2009/0069675 A1    Mar. 12, 2009

(51) Int. Cl.
G06K 9/00 (2006.01)
A61B 8/00 (2006.01)

(52) U.S. Cl. ......................... 382/128; 600/437

(58) Field of Classification Search .......... 382/128–134; 600/407, 410, 425, 437, 441, 445, 454, 455; 128/916, 920, 922, 200.16, 915
See application file for complete search history.

(56) References Cited

U.S. PATENT DOCUMENTS

| 5,349,524 | A | * | 9/1994 | Daft et al. .............. 600/441 |
| 5,443,071 | A |  | 8/1995 | Banjanin et al. |
| 5,445,156 | A | * | 8/1995 | Daft et al. .............. 600/454 |
| 5,467,404 | A | * | 11/1995 | Vuylsteke et al. ........... 382/274 |
| 5,515,852 | A | * | 5/1996 | Karp et al. .............. 600/453 |
| 6,017,309 | A |  | 1/2000 | Washburn et al. |
| 6,045,507 | A |  | 4/2000 | Muzilla et al. |
| 6,071,241 | A |  | 6/2000 | Washburn et al. |
| 6,126,605 | A |  | 10/2000 | Washburn et al. |
| 6,162,176 | A | * | 12/2000 | Washburn et al. ........... 600/454 |
| 6,315,728 | B1 |  | 11/2001 | Muzilla et al. |
| 6,350,241 | B1 |  | 2/2002 | Lifshitz |
| 6,379,306 | B1 |  | 4/2002 | Washburn et al. |
| 6,464,640 | B1 |  | 10/2002 | Guracar et al. |
| 6,679,843 | B2 | * | 1/2004 | Ma et al. .............. 600/441 |
| 6,997,876 | B2 | * | 2/2006 | Mo et al. .............. 600/455 |
| 7,118,532 | B2 |  | 10/2006 | Dubberstein |
| 2007/0038083 | A1 |  | 2/2007 | Srinivasan et al. |
| 2007/0066896 | A1 |  | 3/2007 | Simopoulos et al. |

OTHER PUBLICATIONS

U.S. Appl. No. 11/505,560, filed Aug. 16, 2006.

* cited by examiner

Primary Examiner — Abolfazl Tabatabai

(57) ABSTRACT

Motion imaging in medical diagnostic ultrasound is adaptive. Clutter or threshold processing adapts as a function of data for different locations or for different times. Spatial filtering adapts as a function of data at different spatial locations at a same time. The steering angle may be set as a function of region based on the vessel orientation and maximum velocity. The region of interest for motion imaging may be expanded to counteract, at least in part, a shift due to the steering angle.

20 Claims, 4 Drawing Sheets a)

b)

c)

d)

ADAPTIVE MOTION IMAGING IN MEDICAL DIAGNOSTIC ULTRASOUND IMAGING

BACKGROUND

The present embodiments relate to adaptive motion imaging. In medical diagnostic ultrasound imaging, motion imaging provides visualization of velocity, energy, variance or other motion characteristic of a fluid or tissue.

Medical diagnostic ultrasound imaging systems perform autocorrelation or Doppler processing between sets of received data to determine an average phase shift for fluid or tissue motion imaging. In Doppler processing, the phase shift represents the velocity of tissue or fluid. The energy of the phase shift and/or variance associated with the phase shift may also be used for imaging.

Acoustic energy is transmitted along a scan line, and echoes along the scan line are received. Multiple such transmit and receive events along each scan line are used to determine the phase shift. This phase shift represents the velocity towards or away from the transducer, a one-dimensional velocity. In vessels or other organs, the flow may be in a different direction than the scan line, resulting in inaccurate flow parameter estimation. To counteract this inaccuracy, the user may select settings for the steering angle.

The user sets a region of interest for motion imaging. For example, the region of interest is over a portion or cross section of a vessel. As the steering angle is adjusted, some of the region of interest may be shifted, resulting in the loss of motion imaging for a desired location.

The received signals are filtered prior to estimation of the motion parameters. A wall or clutter filter removes information from slowly moving objects, such as tissue, or removes information from rapidly moving objects, such as blood. A lack of sensitivity to slow or rapid movement due to the filtering may result in desired information being lost. Depending on the type, magnitude or other velocity characteristic, the user may have to reset wall or clutter filter controls for the desired sensitivity.

After estimation, thresholds may be applied, such as velocity and/or energy thresholds. If the velocity or energy for a given spatial location are below the respective thresholds, the velocity is set to a zero or other value. Similarly, spatial filtering may be applied. To avoid flash artifact, different amounts of spatial filtering may be applied depending on a temporal relationship of data. However, the spatial filtering or thresholding may not be optimal for a given situation.

User setting takes time and may be inconvenient. Different preset values for settings may not provide the optimum imaging. This poor plunkability results in longer scan times or sub-optimal imaging quality.

BRIEF SUMMARY

By way of introduction, the preferred embodiments described below include a methods, systems and instructions for adaptive motion imaging in medical diagnostic ultrasound. Clutter or threshold processing adapts as a function of data for different locations or for different times. Spatial filtering adapts as a function of data at different spatial locations at a same time. The steering angle may be set as a function of region based on the vessel orientation and maximum velocity. The region of interest for motion imaging may be expanded to counteract, at least in part, a shift due to the steering angle. Any one or more of these adaptations may be used alone or in combination.

In a first aspect, a method is provided for adaptive motion imaging in medical diagnostic ultrasound. First ultrasound information for a first location at a first time is clutter filtered, thresholded, or both. The clutter filtering, thresholding, or combinations thereof are adapted as a function of second ultrasound information for spatially, temporally, or spatially and temporally adjacent location, time, or location and time, respectively. A velocity image is generated as a function of data output from the adapted clutter filtering, thresholding or combinations thereof.

In a second aspect, a computer readable storage medium has stored therein data representing instructions executable by a programmed processor for adaptive motion imaging in medical diagnostic ultrasound. The instructions are for clutter filtering first ultrasound information for a first location, adapting the clutter filtering as a function of a velocity for spatially, temporally, or spatially and temporally adjacent location, time, or location and time, respectively, and generating a velocity image as a function of data output from the adapted clutter filtering.

In a third aspect, a method is provided for adaptive motion imaging in medical diagnostic ultrasound. Velocities for a first frame of data, the velocities representing different locations, are spatially filtered. The spatial filtering for a first velocity of the first frame of data adapts as function of a second velocity of the first frame of data. A velocity image is generated as a function of an output of the spatially filtering.

In a fourth aspect, a method is provided for adaptive motion imaging in medical diagnostic ultrasound. Acoustic energy is transmitted to each of a plurality of spatial locations from different angles. Velocities for each of the spatial locations for each of the different angles are estimated. A maximum velocity of each of the spatial locations is identified from the velocities of the different angles. Vessel orientations at the spatial locations are determined. Steering angles are set for the spatial locations as a function of the vessel orientations and the maximum velocity.

In a fifth aspect, a method is provided for adaptive motion imaging in medical diagnostic ultrasound. Indication of a first region of interest for velocity is received. A steering angle for the first region of interest is set as a function of a vessel orientation. The first region of interest is expanded to include a second region adjacent a first edge of the first region of interest, where the second region of interest having scan lines with less steering angle than the steering angle of the first region of interest.

The present invention is defined by the following claims, and nothing in this section should be taken as a limitation on those claims. Further aspects and advantages of the invention are discussed below in conjunction with the preferred embodiments. Further claims may be included, such as system or computer readable media claims.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Automatic adjustment of color parameters, like the steering angle, and estimation and display parameters, like the wall filter, spatial filter, and threshold, are provided. User input to adjust the steering angle and filters is removed or reduced, improving the plunkability during colorflow imaging.

Spatially and/or temporally adjacent color samples are used to automatically adjust the color estimation and display parameters. Such color display parameters may include wall filters, spatial filters, thresholds, and steering angle. Spatially and/or temporally adjacent samples are used to adaptively update the clutter filter and threshold selection for increasing low-flow sensitivity and improving color aesthetics. Multiple angle firing is used to identify the local maxima of velocity. Spatial and/or temporal processing of the multi-angle color frames identifies vessel orientation and local steering angles. This allows an automatic regional steering of colorflow, and reduces the need for user control of steering in colorflow. Further, using variable angle steering at region of interest (ROI) edges, the impact of ROI size restrictions imposed by large steering angles may be reduced.

The automatic optimization of the color flow image may improve the plunkability (i.e., reducing color control user interaction) and reduce the time of exams. Color aesthetics and low-flow sensitivity may be improved automatically. The optimization may further assist in diagnosis by providing a larger ROI for steered colorflow imaging.

Figure 1:
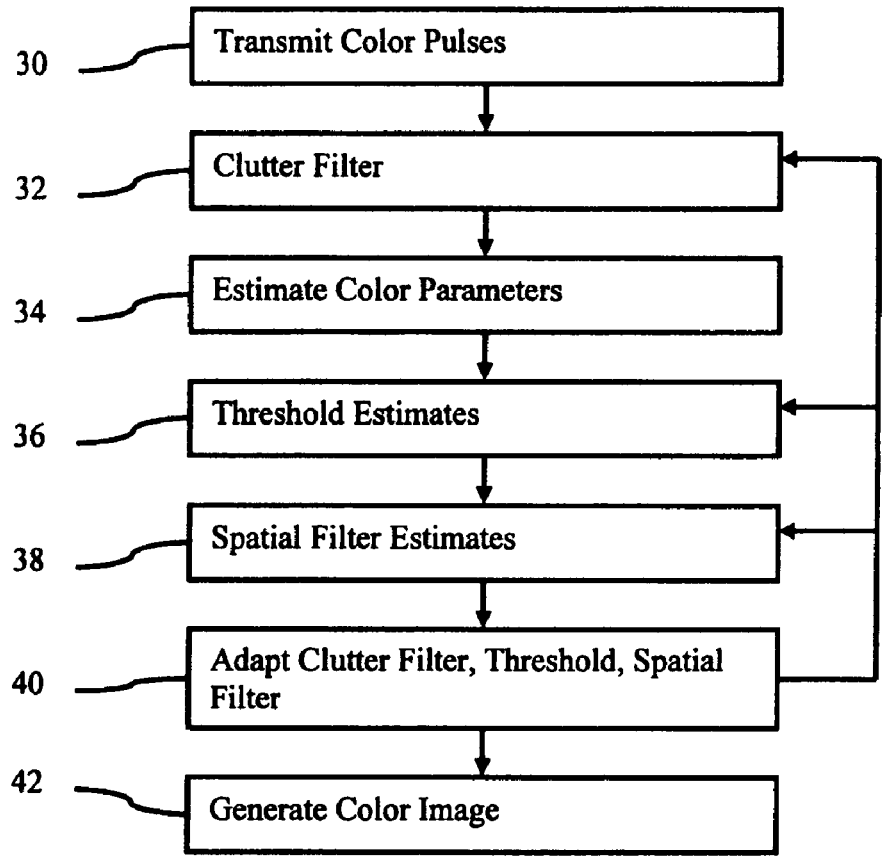
FIG. 1 is a flow chart diagram of one embodiment of a method for adaptive motion imaging of filtering and thresholding in medical diagnostic ultrasound.

FIG. 1 shows a method for adaptive motion imaging in medical diagnostic ultrasound. The method is performed by the system 10 of FIG. 8 or a different system. The acts of FIG. 1 are performed in the order shown or a different order. Additional, different or fewer acts than shown in FIG. 1 may be used. For example, acts 32, 36, and/or 38 are not provided. The acts of FIG. 1 described below may be implemented in different ways. At least one example embodiment is provided below, but other embodiments are possible.

The process is initiated by a user or in response to detecting a triggering event. For example, the transmitting of act 30 is started in response to user activation of motion imaging or designation of a region of interest for velocity, energy, and/or variance imaging.

The adaptation of act 40 may be initiated at the same time, periodically, in response to user input, or in response to detecting a triggering event. For example, the user depresses a button once or whenever the velocity image appears to have undesired velocity sensitivity or scan angle. As another example, the system detects movement of the transducer or a change in the region being scanned. As a result, new adaptations are triggered. In another example, the adaptation is continuous or periodic.

Motion imaging includes Doppler imaging, but temporal correlation or other processes may be used to estimate motion. Motion imaging may be referred to a color imaging since the detected motion is displayed using color modulation. A gray scale B-mode image may be combined with, overlaid on, or partially covered by the color information. In other embodiments, the motion information is displayed in gray scale. The motion may be for tissue, contrast agents, and/or fluid. Velocity and flow imaging are specific types of motion imaging.

FIG. 1 provides a method for automatic color parameter identification. The color parameters include wall or clutter filtering, thresholding, and spatial filtering, but may be a sub-set or include additional parameters.

In act 30, motion imaging pulses are transmitted. Any now known or later developed pulse sequences may be used. Motion pulses are a sequence of at least two (flow sample count) transmissions along each scan line. Any pulse repetition frequency, flow sample count, and pulse repetition interval may be used. The echo responses to the transmissions of the sequence are used to estimate velocity, energy (power), and/or variance at a given time. The transmissions along one line may be interleaved with transmissions along another line. With or without interleaving, the estimates for a given time are acquired using transmissions from different times, but substantially close to the time represented by the estimates.

By scanning along a plurality of scan lines, a frame of data representing the region of interest at a same time is acquired. The estimates from different scan lines may be acquired sequentially, but rapidly enough to represent a same time from a user perspective. Multiple scans are performed to acquire estimates for different times. For every image pixel in a region of interest, information from spatially and temporally adjacent pixels is available. The information may be samples prior to estimation, estimated samples in a polar coordinate format, estimates prior to color (RGB) conversion, estimates after color conversion, estimates prior to scan conversion, and/or estimates after scan conversion. For example, color and scan converted information, such as associated with displayed images, is used. As another example, estimates after scan conversion and prior to color conversion are used.

In one embodiment, the signals are for scan lines in a full sampling of a color or velocity region of interest. In another embodiment, the obtained signals correspond to sparse sampling of the velocity region of interest. For example, a sparsely sampled pilot velocity sample group (e.g., every other, fourth, eighth, sixteenth or other number scan lines 11 with full or sparse range sampling) is obtained. The transmissions have any desired F-number, but low F-numbers may be used, such as with fully sampled scanning for adaptation.

In act 32, signals received in response to the transmissions of act 30 are clutter filtered. The signals for each spatial location are transferred from buffers or a memory (e.g., corner turning memory) to a filter. The filter pass band, rise time, rejection band and other characteristics are set to reduce the contribution from undesired information. For example, the signals are filtered to remove or reduce information from slowly or non-moving tissue, leaving signals from moving fluid. As another example, signals from tissue remain, and signals from more rapidly moving fluid are reduced. In other examples, signals associated with motion remain, but signals associated with possible noise or lack of motion are removed. Any now known or later developed clutter filtering may be used.

The clutter filtering is of signals in the pulse sequence for estimating motion at a given time. A given signal may be used for estimates representing different times, such as associated with a moving window for clutter filtering and estimation. Different filter outputs are used to estimate motion for a location at different times.

In act 34, the motion is estimated. For each spatial location, the velocity, energy (power), and/or variance are estimated. Doppler processing, such as autocorrelation, may be used. In other embodiments, temporal correlation may be used. Estimates are formed for different groupings of received signals, such as completely separate or independent groupings or overlapping groupings. The estimates for each grouping represent the spatial location at a given time. Multiple frames of estimates may be acquired to represent the region of interest at different times.

In act 36, the estimates are thresholded. Thresholds are applied to the velocities. For example, a low velocity threshold is applied. Velocities below the threshold are removed or set to another value, such as zero. As another example, where the energy is below a threshold, the velocity value for the same spatial location is removed or set to another value, such as zero. Alternatively, the estimated velocities are used without thresholding.

In act 38, the estimates are spatially filtered. For example, the thresholded velocities of a frame of data are spatially filtered. Velocities from different spatial locations are input to the filter, and a filtered output is provided. Any spatial filter may be used, such as 5-7 tap filter in at least one dimension. The filter may be programmable. The filter is one, two, or three-dimensional. In alternative embodiments, spatial filtering is not provided, is provided prior to thresholding, or is provided before estimation.

In act 40, the clutter filtering (act 32), thresholding (act 36), and/or spatial filtering (act 38) are adapted as a function of received signals. The adaptation occurs at a same time or different times for the different acts. The adaptation alters the filtering and/or thresholding for subsequent information. Alternatively, the information used to determine an adaptation is first processed or reprocessed after adaptation.

In one embodiment, the clutter filter pass band and at least one threshold adapt based on spatial and/or temporal ultrasound information. The ultrasound information is a velocity, receive signal before estimation, or information from elsewhere between acquisition and display. For clutter filtering, any characteristic of the clutter filter may be altered. A rejection region, a rise time, or both change as a function of feed forward or feed back information.

For example, a velocity at one location for a given time is determined from clutter-filtered data. A velocity and/or energy of a spatially adjacent location and/or temporally adjacent time is determined. The reject band of a clutter filter to be applied to the one location is reduced if the spatially or temporally adjacent velocity and/or energy is lower than the velocity and/or energy of the one location. Rather than comparing the estimates, a threshold may be applied. If the velocity and/or energy of a spatially and/or temporally adjacent color pixel is low, then the clutter-filter rejection band is reduced (i.e., the pass-band is increased), and the thresholds are reduced. The reductions may improve low-velocity sensitivity. In some cases, there could be a velocity bias due to insufficient clutter-rejection, such as associated with rise time. If the adjacent spatial and/or temporal information have higher velocities, then the clutter-filter reject band may be increased to reduce velocity bias. The reduction or increase may be by any amount, such as about 10%.

The rejection band and a threshold level (e.g., velocity threshold) are increased if the spatially or temporally adjacent velocity is higher than the velocity for the one location. Alternatively, if the velocity (and energy) of a spatially and/or temporally adjacent information is high as compared to a threshold, then the clutter-filter reject band is increased (i.e., decrease the pass band), and the thresholds are increased to reduce flash. Any number of different clutter filters may be provided, such as adapting between two different filters. In one embodiment, a range of filters are provided based on a range of data levels, combinations of data, and/or number of iterations of adapting.

The adaptation is performed as a function of ultrasound information for spatially, temporally, or spatially and temporally adjacent location, time, or location and time, respectively. Information for more than one spatially or temporally adjacent location may be used for adapting the clutter filter and/or thresholds. For example, a median, average, maximum, minimum, or other selection criterion is used for ultrasound information from a plurality of adjacent locations, such as identifying any value in a 3×3 spatial region or one or more temporally adjacent regions that satisfy the adjustment or comparison criteria.

In one embodiment, the spatial filtering of act 38 adapts as a function of spatially adjacent locations. The filtering adapts for different filtering of sequential frames of data, regions within a frame, or different spatial locations. For example, the filter applied to each spatial location adapts independently.

Velocities are spatially filtered, but other types of estimates or ultrasound information may be spatially filtered. The adaptation is a function of neighboring velocities, but other types of estimates or ultrasound information may be used.

In one embodiment, an extent of the spatial filtering is modified as a function of a sign of a neighboring velocity and an energy magnitude corresponding to the neighboring velocity. The spatial filtering is decreased if the sign is different than for other velocities in a filter kernel and a threshold difference in energy values of the filter kernel is satisfied. If there is a large discrepancy in the energy values and the velocity sign changes, it is likely to indicate boundaries. The adaptation of clutter filtering and thresholding may avoid voids or holes in the velocity data so that the discrepancy in energy values and change in velocity sign is not caused by undesired comparison. The spatial filtering decrease at those pixels may preserve boundaries (reduce loss of spatial resolution at boundaries).

A length of a filter kernel is reduced if the sign is different than for other velocities in the filter kernel. Any reduction along one or more dimensions may be used, such as reducing a 5×5 kernel to 3×3. The filtering may be changed by a change in the kernel or a change in one or more weights. The reduction in length may reduce artifacts (aliasing) due to filtering and preserve the velocity reversal.

Where the sign does not change, or where the sign does not change and only small differences in energy exist, increased filtering or larger kernels may be used. More than two options may be provided, such as providing three or more (e.g., five) different filter kernels or pass bands based on sign and/or thresholds.

In act 42, a color image is generated. For example, a velocity image is generated as a function of data output from the adapted clutter filtering, thresholding, spatial filtering, or combinations thereof. The motion imaging is for a sparse or full sampling of the velocity region of interest. Color values are displayed for the regions of interest and not for other spatial locations. The signals used for adaptation may or may not be used for imaging.

The image represents velocity, energy, and/or variance. The image may be overlaid on a B-mode image. As additional color images are available, the display is updated to display the additional color images.

Figure 5:
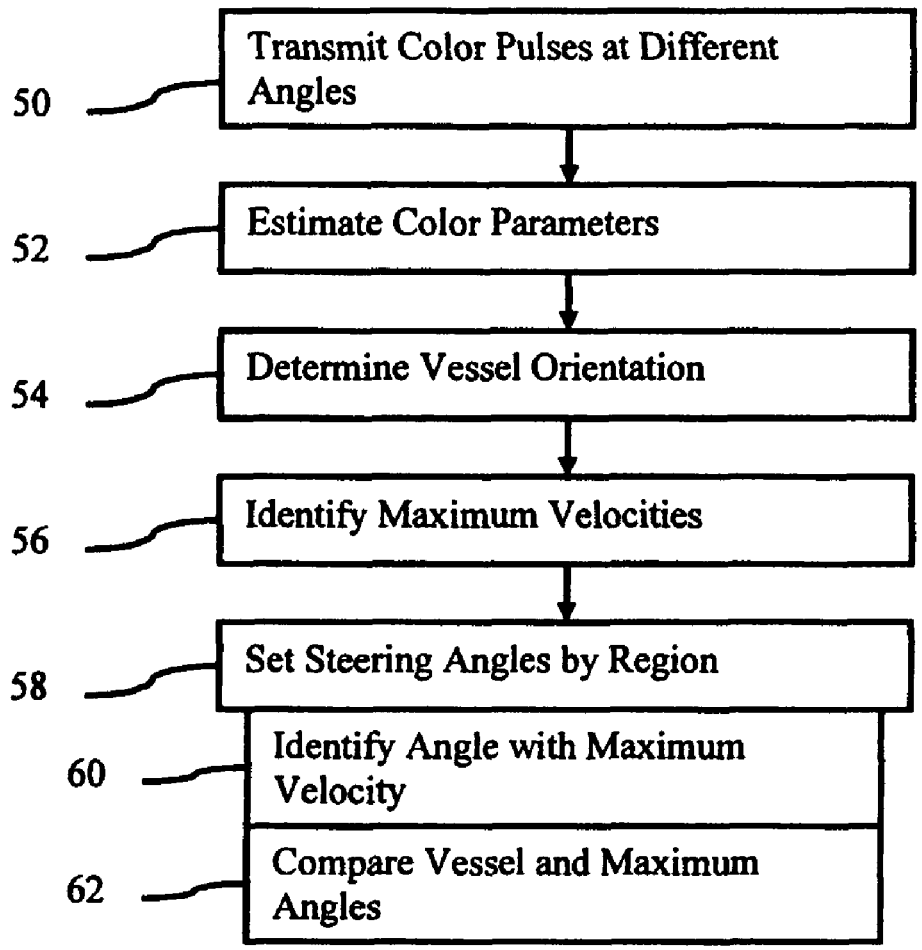
FIG. 5 is a flow chart diagram of one embodiment of a method for adaptive motion imaging of steering angle in medical diagnostic ultrasound.

FIG. 5 shows a method for adaptive motion imaging in medical diagnostic ultrasound. The method is performed by the system 10 of FIG. 8 or a different system. The acts of FIG. 5 are performed in the order shown or a different order. Additional, different or fewer acts than shown in FIG. 5 may be used. The acts of FIG. 5 described below may be implemented in different ways. At least one example embodiment is provided below, but other embodiments are possible.

FIG. 5 shows a method for adapting by automatically setting steering angles for different regions of a scan region. The steering angle is set to be closer to an angle or orientation of flow within a vessel or direction of movement. The resulting velocities may be closer to actual velocities. This method is used with or without the velocity data output from the method of FIG. 1. Other velocity processing may be provided, such as non-adaptive processes for outputting estimated velocities.

In act 50, motion pulses are transmitted. The same or different pulses described in act 30 of FIG. 1 may be used. Fully sampled transmission and reception may be used. Alternatively, low F-number and/or sparsely sampled pulses are transmitted and received.

Multiple frames of data are acquired, such as two or more. Each frame of data corresponds to a different scan line angle. For example, delay, phasing, and/or apodization are used to transmit beams at different angles. The receive beams are also formed at the different angles. Alternatively, just the transmit or just the receive beamformation occurs at the different angles. In a linear scan format, each frame of data corresponds to parallel beams formed along scan lines at different angles relative to the transducer. In a sector or Vector® scan format, the beams may not be parallel, but have a bias or general angle for the scan lines in a frame data. A different bias or general angle is applied for each from of data. In one example, at least three frames of data are acquired, one with a positive angle, one with a negative angle, and one with a zero angle. FIGS. 2a, 3a, and 4a each show scan lines at the three different angles. Each frame of data is formed with multiple scan lines associated with the offset angle.

In act 52 of FIG. 5, color parameters are estimated. For example, velocities are estimated for each of the spatial locations for each of the different angles. Due to the angle difference, each frame of data may represent a different overall region, but the different regions overlap. Velocities are estimated for each frame of data.

In act 54, the vessel or motion orientation is determined. The determination provides one orientation for the entire region of interest or provides different orientations for different respective spatial locations or regions. Since the vessel may not be straight throughout the color region of interest, the different orientations of the vessel are determined as a function of spatial location.

Any technique to determine vessel orientation may be used, such as a region thinning, boundary detection, peak velocity, curve fitting, or center of mass. In one embodiment, a largest velocity for each of the spatial locations is identified from the velocities of the different angle frames of data. A frame of the maximum velocity at each spatial location is formed from the velocities of two or more frames of data. The spatial velocity-maximum frame of data is decimated by any desired amount. Decimation may reduce calculation. No or any amount of decimation may be provided. The decimated frame of data is thresholded (using energy and/or velocity thresholds) and binarized. For example, an energy threshold is applied. Values above the threshold are set to one and values below are set to zero. Binarizing may identify locations more likely associated with the flow in the vessel. Three or more discrete values may be used in alternative embodiments, such as to provide for weighted identification of the vessel orientation. A morphological process, such as skeletonization, is applied to the binary image. The morphological process identifies the vessel orientation ($\phi_{vessel}$) at different locations along the vessel. Since the binary frame of data associated with the largest velocities is used, the skeleton or indication of the vessel orientation may more likely avoid inaccuracies due to other data.

The velocities used for vessel orientation may be subject to aliasing. The user or a processor sets the scale to minimize aliasing. Aliasing may be acceptable. Alternatively, the phase unwrapping of act 56 is performed and then act 54 is repeated in an iterative process.

In act 56, a maximum velocity for each of the spatial locations is identified. The maximum velocities are determined for each frame of data corresponding to the different angles. The maximum velocity identified takes into account aliasing and velocity-sign discrepancies. Any technique to correct aliasing may be used, such as adaptively setting the scale or any phase unwrapping.

Figure 2:
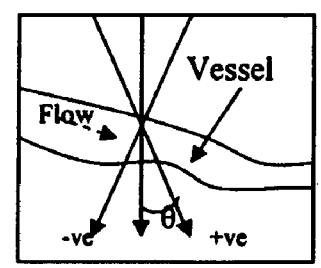
FIGS. 2-4 are graphical representations showing examples related to aliasing.
Figure 2:
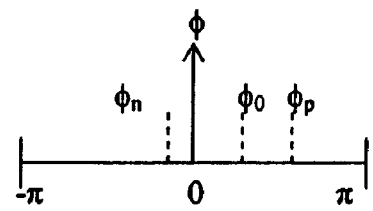
Figure 2:
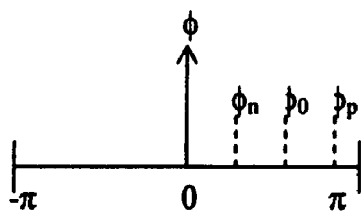
Figure 2:
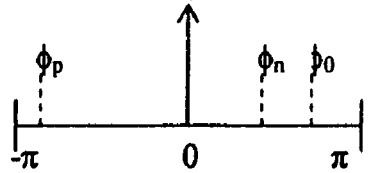
Figure 3:
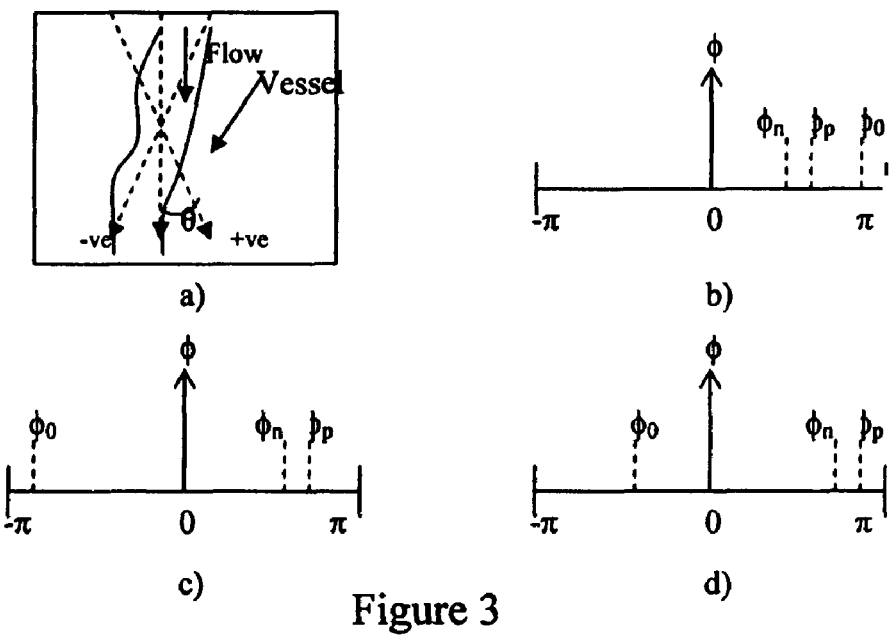
Figure 4:
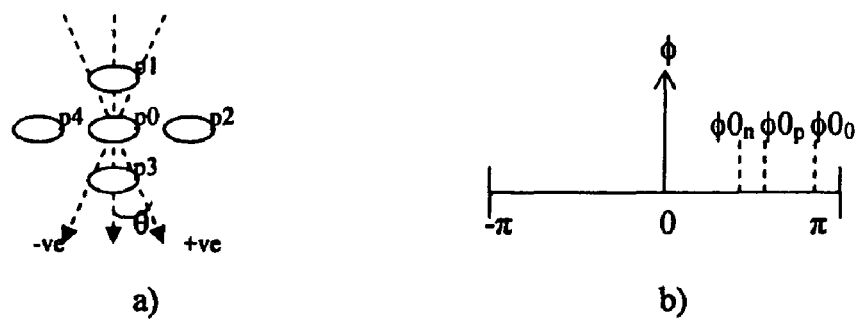

FIGS. 2-4 graphically represent one embodiment of phase unwrapping. FIG. 2a shows velocities that increase from a negative angle (−ve) to the zero-angle and increase from the zero-angle to the positive-angle (+ve). This relationship results from the relative position of the flow direction to the scan line angles. FIG. 2b shows a case where aliasing does not occur but the negative angle is more than 90 degrees relative to the vessel orientation. FIG. 2c shows a case where the velocity increases from the negative angle to the zero angle and from the zero angle to the positive angle. FIG. 2d shows a case where aliasing occurs for the positive angle and the abs($\phi_p$)>abs($\phi_0$).

The local vessel orientation is compared to the insonification angle. If the relative angle is greater than 90 degrees, any velocity reversal is identified. FIG. 2b shows the negative velocity as having a different sign, indicating reversal. If for a given insonification angle (e.g., positive angle), the estimated velocity sign indicates a velocity reversal, then the velocity ratios are checked for reasonable agreement to the angular relationship $$\left(\frac{\phi_n}{\phi_p} = 2\frac{\phi_0}{\phi_p}\cos\theta - 1\right),$$

where $\Phi_n$ is the negative velocity, $\Phi_0$ is the zero velocity, $\Phi_p$ is the positive velocity, and θ is the angle between the zero and negative or positive scan lines (e.g., 20%). Any threshold may be used for reasonable agreement, such as within 10-20%. If there is a reasonable agreement, then the angle from the other two insonification angles based on maximum velocity and the corresponding maximum velocity are chosen. In the example of FIG. 2, the positive angle is selected. If the velocity ratios are not in reasonable agreement, the spatial neighbors are used to determine the angle and corresponding maximum velocity as explained below in the example of FIG. 4.

The estimated velocities may have a same sign, such as shown in FIG. 2c. If the velocity ratios are in reasonable agreement (e.g., 10-20%) to the angular relationship $$\left(\frac{\phi_n}{\phi_p} = 2\frac{\phi_0}{\phi_p}\cos\theta - 1\right),$$

the absence of aliasing is indicated. Aliasing may occur in other situations, such as shown in FIG. 2d. If aliasing occurs, the velocity ratio is not in reasonable agreement with the angular relationship.

If there is aliasing, then phase-unwrapped velocities are checked to see the agreement with the angular relationship. Phase unwrapping is provided by adding $2\pi$ to the velocity with a different sign. The maximum absolute velocity (unwrapped in the case of aliasing) and the angle that corresponds to the maximum is chosen.

FIG. 3a shows a case where the maximum of the velocity occurs in the zero angle direction. FIG. 3b shows a case where the velocity increases from the negative angle to positive angle, and from the positive angle to the zero angle. FIG. 3c shows a case where aliasing occurs for the −zero angle and $abs(\phi_0) > abs(\phi_p)$. FIG. 3d shows a case where aliasing occurs for the zero angle and $abs(\phi_0) < abs(\phi_p)$.

For the example of FIG. 3, the velocity ratios are checked against the angular relationship. If there is reasonable agreement, the absence of aliasing is indicated. The maximum absolute velocity (unwrapped in the case of aliasing) and the angle that corresponds to the maximum are chosen If there is poor agreement with the angular relationship, then spatially adjacent neighbors are used to resolve the velocity phase ambiguities. FIG. 4a shows scan lines at the −ve, 0 and +ve angles. Five adjacent velocities p0, p1, p2, p3, and p4 are shown. FIG. 4b shows the velocity increasing from the negative angle to the positive angle, and the positive angle to the zero angle for the center velocity p0. The mean velocity for the four adjacent velocities (p1, p2, p3, and p4) are computed for the three angles as:

$$\phi m_0 = (\phi 1_0 + \phi 2_0 + \phi 3_0 + \phi 4_0)/4$$

$$\phi m_p = (\phi 1_p + \phi 2_p + \phi 3_p + \phi 4_p)/4$$

$$\phi m_n = (\phi 1_n + \phi 2_n + \phi 3_n + \phi 4_n)/4$$

The minimum of the difference between $\phi 0$ and $\phi m$ in velocities is computed over the angles, where $\phi 0$ is the velocity of interest (e.g., p0). The minimum difference from the three possible differences is represented by the index:

$$I = \min(abs(\phi m_0 - \phi 0_0), abs(\phi m_p - \phi 0_p), abs(\phi m_n - \phi 0_n))$$

$$I \subset (0, p, n)$$

The ratio of $\phi_1/\phi_0$ is compared to $\phi_1/\phi_m$ to identify the largest discrepancy, and the phase is corrected if the discrepancy exceeds $\pi$. If the comparison indicates a sufficient difference, such as $\pi$, the velocity is unwrapped or corrected for aliasing. The ratio comparison and corresponding unwrapping to correct phase is represented as follows:

$$\text{if}\left(\frac{\phi 0_1}{\phi 0_0} - \frac{\phi 0_1}{\phi m_0} > \pi\right) \text{unwrap } \phi 0_0$$

$$f\left(\frac{\phi 0_1}{\phi 0_p} - \frac{\phi 0_1}{\phi m_p} > \pi\right) \text{unwrap } \phi 0_p$$

$$f\left(\frac{\phi 0_1}{\phi 0_p} - \frac{\phi 0_1}{\phi m_n} > \pi\right) \text{unwrap } \phi 0_n$$

The maximum absolute velocity and the angle that corresponds to the maximum is chosen. A maximum velocity and corresponding angle is identified for each spatial location in or for two or more portions of the region of interest. For energy, aliasing is not an issue and therefore the maximum energy and the corresponding angle is chosen.

In act 58, steering angles for spatial locations are set. The steering angles are a function of the vessel orientations and one or more of the maximum velocities. In one embodiment, acts 60 and 62 are performed to set the steering angle. In other embodiments, different acts may be used.

In act 60, the maximum velocities identified in act 56 are used to determine the angle. The angle corresponding to the maximum velocity is identified for each of the spatial locations. For example, a frame of data corresponding to the maximum velocities is formed. Another frame of data corresponding to the angles associated with the maximum velocities is formed. For every spatial location or region, spatial smoothing (e.g., median filtering) of the angles in the angle frame of data is performed. For example, a 3×3 neighborhood or kernel is applied. The most frequently occurring angle within the region is used for the center location of the kernel. The spatial filtering reduces local discontinuities. The spatial velocity maximum frame of data is also spatially smoothed using a same or different filter, such as a boxcar filter.

To avoid overlapping or overly complicated scan patterns due to different steering angle settings, the steering angle may be set for regions larger than each spatial location. Decimation or other process may be used. In another example, the skeleton of the vessel is divided into regions and a mean or median of the angles from the angle frame of data is determined for each region. As another example, a median in different 8×8, 16×16 or other sized regions is determined, providing regions of 64, 256, or other number of spatial locations.

In act 62, the vessel orientation in each region is compared to the identified angle. The regions correspond to spatial locations or group of spatial locations. The steering angle for each region is set as a function of the comparison. For example, each region within the region of interest is scanned with beams along the flow direction or closer to the flow direction. The transducer position relative to the vessel or region of interest may limit the possible angles. A maximum steering angle or other angle matching the flow direction is determined for scanning each region.

In one embodiment, an iterative or stepped adjustment is provided. The angle is incrementally improved. The adjustment may not result in the maximum angle or the same angle as the flow direction, but improves the angle as compared to prior to incrementing. For example, the regional steering angle and the vessel orientation are compared. Any difference is corrected. The comparison and correction are represented as:

$$\text{if}(abs(\phi_{steering}) < (abs(\phi_{vessel}))/2) \text{ increase } \phi_{steering} \text{ by } \Delta_{steering}$$

$$\text{if}(abs(\phi_{steering}) > (abs(\phi_{vessel}))/2) \text{ decrease } \phi_{steering} \text{ by } \Delta_{steering}$$

where $\Delta_{steering}$ is an incremental angle adjustment, such as +/−10 degrees or other adjustment.

The method of FIG. 5 may be repeated. For example, a different pulse repetition frequency (PRF) is used in each repetition to improve the robustness with respect to different velocity scales.

Figure 7:
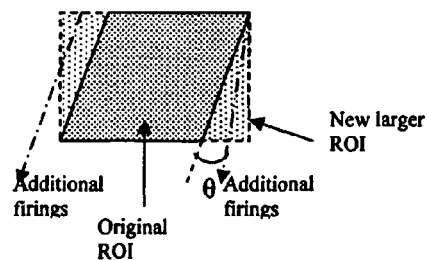
FIG. 7 is a graphical representation of a region of interest with expanded portions according to one embodiment.

The steering, whether automatically set or set by the user, may result in a region of interest not covering a desired area or volume. FIG. 7 shows an original region of interest as a parallelogram. On each edge of the original region of interest is an area that a user may desire to be in the region of interest. The original region of interest may be expanded with additional firings.

Figure 6:
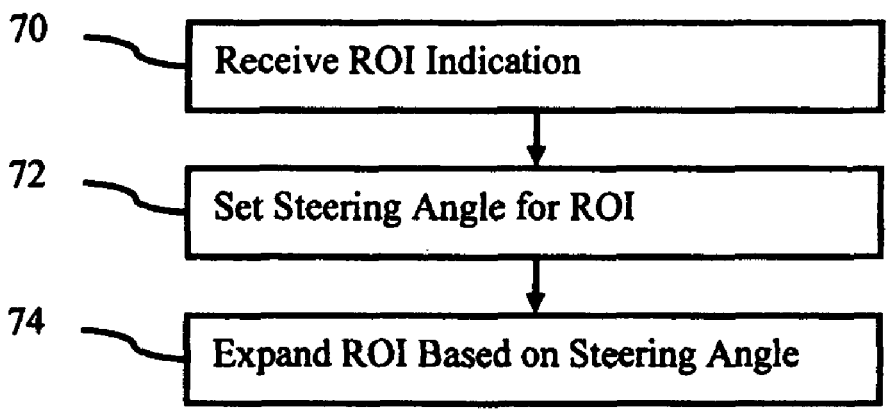
FIG. 6 is a flow chart diagram of one embodiment of a method for adaptive motion imaging with an expanding region of interest in medical diagnostic ultrasound.

FIG. 6 shows a method for adaptive motion imaging in medical diagnostic ultrasound. The method is performed by the system 10 of FIG. 8 or a different system. The acts of FIG. 6 are performed in the order shown or a different order. Additional, different or fewer acts than shown in FIG. 6 may be used. The acts of FIG. 6 described below may be implemented in different ways. At least one example embodiment is provided below, but other embodiments are possible.

FIG. 6 shows a method for adapting by expanding a region of interest. Additional scan lines with a same or different angles than for scan lines of the original region of interest are used. The region of interest is expanded laterally along one or more edges. For example and as shown in FIG. 7, the region of interest is expanded to have more area and be more rectangular. Other expansions and/or other shapes of the region may be used, such as maintaining the parallelogram shape.

This method is used with or without the velocity data output from the method of FIG. 1 and/or the steering angles determined in the method of FIG. 5. Other velocity processing may be provided, such as non-adaptive processes for outputting estimated velocities. Other steering processes may be provided.

In act 70, a region of interest for motion imaging is received. User input, border detection, and/or other process indicate the region of interest. For example, the user traces a vessel region or heart chamber. As another example, the user places points to indicate corners of the region of interest. In another example, the user alters or assists border detection for semiautomatic determination of the region of interest.

In act 72, the steering angle is set for the region of interest. The steering angle is set as a function of a vessel orientation. For example, the steering angle is set to be more parallel with a direction of flow, such as using the method of FIG. 5. FIG. 7 shows the region of interest having side or lateral edges parallel to the scan lines. The region of interest is angled to be along the scan lines. The steering angle may alter the region of interest. Alternatively, the region of interest is initially determined as a function of the steering angle. The angle is set in act 72 as part of or before receiving an indication of the region of interest in act 70.

In act 74, the region of interest is expanded to include at least one region adjacent an edge of the first region of interest. Other expansions may be provided, such as expanding along two opposite or adjacent edges. The expansion may be relative to a vessel or other imaged structure.

The expansion includes acquiring data along additional scan lines. For example, B-mode data is acquired for at least regions outside the region of interest. Data for estimating motion parameters is acquired along scan lines in the region of interest. For any expansion, data for estimating motion parameters is acquired for scan lines in the expanded area. The transmission and reception discussed above for acts 30 and/or 50 are performed for the region of interest, including the expanded areas.

The scan lines for expansion are parallel to the scan lines in the region of interest or the edge of the region of interest. For example, FIG. 7 shows additional scan lines to the left of the original region of interest.

The scan lines may have a different angle than one or more scan lines in the region of interest. For example, FIG. 7 shows additional scan lines to the right of the original region of interest. These additional scan lines have a same origin, but different angles. The additional scan lines have less steering angle than the steering angle of the original region of interest. The decrease in steering angle at the edge increases the region of interest. In alternative embodiments, different origins may be used. Greater steering angles than of the region of interest may be used, such as for the expansion on the left side of FIG. 7.

In the region based steering of the method of FIG. 5 and/or the scan lines with different angles in the region of interest of the method of FIG. 6, the angle difference may skew the velocities. Scan lines more along the direction of flow may have higher velocities. To make the representation more uniform, the velocities along one or more scan lines are angle corrected. For example, all of the velocities along all of the scan lines are angle corrected using the local vessel orientation. For angle and direction correction, the vessel orientation and the angle between the lines $$\left(\phi_{angle-correct} = \phi \frac{\cos(\theta_{vessel} + \theta)}{\cos\theta_{vessel}}\right)$$

may be used. Velocities from adjacent spatial locations may be used to fill-in holes and avoid aliasing artifacts.

As another example, the velocity correction accounts for the difference in scan line angles rather than correction based on the direction of motion. In the example of expansion of the right edge of the region of interest in FIG. 7, the angle between the lines $$\left(\phi_{angle-correct} = \frac{\phi}{\cos\theta}\right)$$

is used for angle correcting the velocities along the expansion scan lines.

Figure 8:
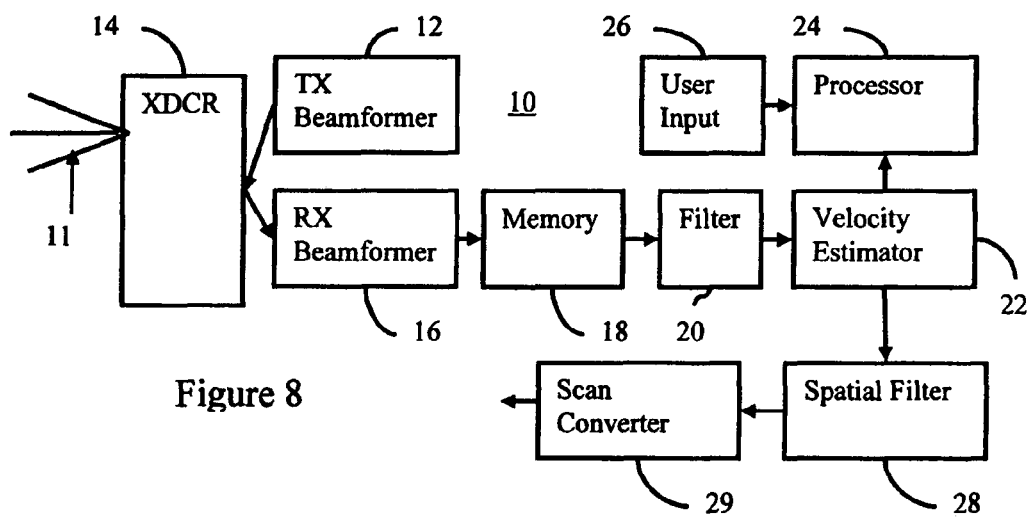
FIG. 8 is a block diagram of one embodiment of a system for adaptive motion imaging in medical diagnostic ultrasound.

FIG. 8 shows one embodiment of a system 10 for adaptive motion imaging in medical diagnostic ultrasound. The system 10 includes a transmit beamformer 12, a transducer 14, a receive beamformer 16, a memory 18, a filter 20, a velocity estimator 22, a spatial filter 28, a scan converter 29, a processor 24, and a user input 26. Additional, different or fewer components may be provided. For example, the system includes the velocity estimator 22 and processor 24 without the front-end components such as the transmit and receiver beamformers 12, 16. As another example, a display is provided. In one embodiment, the system 10 is a medical diagnostic ultrasound system. In an alternative embodiment, the system 10 is a computer or workstation. In yet another embodiment, the velocity estimator 22 is part of a medical diagnostic ultrasound system or other medical imaging system, and the processor 24 is part of a separate workstation or remote system.

The transmit beamformer 12 is shown separate from the receive beamformer 16. Alternatively, the transmit and receive beamformers 12, 16 may be provided with some or all components in common. Operating together or alone, the transmit and receive beamformers 12, 16 form beams of acoustic energy for scanning a one, two or three-dimensional region. One or more scan lines 11 are scanned. Vector®, sector, linear or other scan formats may be used. A single receive beam is generated for each transmit beam. Alternatively, two or more receive beams are generated for each transmit beam.

The transmit beamformer 12 is a processor, delay, filter, waveform generator, memory, phase rotator, digital-to-analog converter, amplifier, combinations thereof or any other now known or later developed transmit beamformer components. In one embodiment, the transmit beamformer 12 digitally generates envelope samples. Using filtering, delays, phase rotation, digital-to-analog conversion and amplification, the desired transmit waveform is generated. Other waveform generators may be used, such as switching pulsers or waveform memories.

The transmit beamformer 12 is configured as a plurality of channels for generating electrical signals of a transmit waveform for each element of a transmit aperture on the transducer 14. The waveforms are unipolar, bipolar, stepped, sinusoidal or other waveforms of a desired center frequency or frequency band with one, multiple or fractional number of cycles. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles and combinations thereof. A scan line focus is generated based on these beamforming parameters.

The transducer 14 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, combinations thereof or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The receive beamformer 16 is a preamplifier, filter, phase rotator, delay, summer, base band filter, processor, buffers, memory, combinations thereof or other now known or later developed receive beamformer components. The receive beamformer 16 is configured into a plurality of channels for receiving electrical signals representing echoes or acoustic energy impinging on the transducer 14. A channel from each of the elements of the receive aperture within the transducer 14 connects to an amplifier and/or delay. An analog-to-digital converter digitizes the amplified echo signal. The digital radio frequency received data is demodulated to a base band frequency. Any receive delays, such as dynamic receive delays, and/or phase rotations are then applied by the amplifier and/or delay. A digital or analog summer combines data from different channels of the receive aperture to form one or a plurality of receive beams. The summer is a single summer or cascaded summer. In one embodiment, the beamform summer is operable to sum in-phase and quadrature channel data in a complex manner such that phase information is maintained for the formed beam. Alternatively, the beamform summer sums data amplitudes or intensities without maintaining the phase information.

The receive beamformer 16 is operable to form receive beams in response to the transmit beams. For example, the receive beamformer 16 receives one or two receive beams in response to each transmit beam. The receive beams are collinear, parallel and offset or nonparallel with the corresponding transmit beams. The receive beamformer 16 outputs image data, data representing different spatial locations of a scanned region. Once the channel data is beamformed or otherwise combined to represent spatial locations along the scan lines 11, the data is converted from the channel domain to the image data domain.

For imaging motion, such as tissue motion or fluid velocity, multiple transmissions and corresponding receptions are performed for a substantially same spatial location. Phase changes between the different receive events indicate the velocity of the tissue or fluid. A velocity sample group corresponds to multiple transmissions for each of a plurality of scan lines 11. The scan lines 11 may be sparsely sampled, such as scanning every eighth, tenth or sixteenth scan line 11 multiple times for each velocity sample grouping. The number of times a substantially same spatial location, such as a scan line 11, is scanned within a velocity sample group is the velocity sample count. The transmissions for different scan lines 11, different velocity sample groupings or different types of imaging may be interleaved. The amount of time between transmissions to a substantially same scan line 11 within the velocity sample count is the pulse repetition interval or pulse repetition frequency. Pulse repetition interval is used herein, but includes the pulse repetition frequency.

The memory 18 is video random access memory, random access memory, removable media (e.g. diskette or compact disc), hard drive, database, corner turning memory or other memory device for storing data or video information. In one embodiment, the memory 18 is a corner turning memory of a motion parameter estimation path. The memory 18 is operable to store signals responsive to multiple transmissions along a substantially same scan line. The memory 22 is operable to store ultrasound data formatted in an acoustic grid, a Cartesian grid, both a Cartesian coordinate grid and an acoustic grid, or ultrasound data representing a volume in a 3D grid.

The filter 20 is a clutter filter, finite impulse response filter, infinite impulse response filter, analog filter, digital filter, combinations thereof or other now known or later developed filter. In one embodiment, the filter 20 includes a mixer to shift signals to base band and a programmable low pass filter response for removing or minimizing information at frequencies away from the base band. In other embodiments, the filter 20 is a low pass, high pass or band pass filter. The filter 20 identifies velocity information from slower moving tissue as opposed to fluids or alternatively reduce the influence of data from tissue while maintaining velocity information from fluids. The filter 20 has a set response or may be programmed, such as altering operation as a function of signal feedback or other adaptive process. In yet another embodiment, the memory 18 and/or the filter 20 are part of the velocity estimator 22.

The velocity estimator 22 is a Doppler processor or cross-correlation processor for estimating velocity. In alternative embodiments, another device now known or later developed for estimating velocities from any or various input data may be provided. The velocity estimator 22 receives a plurality of signals associated with a substantially same location at different times and estimates a Doppler shift frequency, based on a change or an average change in phase between consecutive signals from the same location. Velocity is calculated from the Doppler shift frequency. Alternatively, the Doppler shift frequency is used as a velocity. The velocity estimator 22 outputs velocity data that may include aliased information or velocities. Where an actual velocity is outside of the velocity scale (i.e. PRI) or range as a function of the Nyquist sampling frequency, the velocity data is aliased. Velocity information for a particular spatial location or a plurality of spatial locations (e.g. scan lines 11) is output. More than one signal sample may be provided for any given spatial location. For example, 1 to 12 samples are output for each spatial location. The velocity estimator 22 may also estimate energy and/or variance for each velocity estimate.

The velocity estimator 22 may apply one or more thresholds to identify sufficient motion information. For example, velocity and/or energy thresholding for identifying velocities is used. In alternative embodiments, a separate processor or filter applies thresholds.

The spatial filter 28 is a finite impulse response filter, infinite impulse response filter, analog filter, digital filter, combinations thereof or other now known or later developed filter. In one embodiment, the spatial filter 28 includes a mixer to shift signals to base band and a programmable low pass filter response for removing or minimizing information at frequencies away from the base band. In other embodiments, the spatial filter 28 is a low pass, high pass or band pass filter. The spatial filter 28 may include a memory for storing data representing different spatial locations.

The scan converter 29 converts data from a polar coordinate format to a Cartesian coordinate format. Interpolation, nearest neighbor, or other conversion may be used. The scan converter 29 may include a look-up table or processor for converting motion estimates to color (e.g., RGB).

The user input 26 is a keyboard, buttons, joystick, trackball, mouse, sliders, touch pad, combinations thereof or other now known or later developed input device. The user input 26 provides signals to the processor 24 or other components of the system 10 in response to user activation. For example, the signals from the user input 26 control configuration of the system 10 for velocity or tissue motion imaging. As another example, a button or other device is provided for single or one time activation of automated adaptation. As yet another example, the user input 26 is used to select velocity or tissue motion imaging with periodic adaptation for motion imaging. The user input 26 may be used to designate or assist in processor based designation of a region of interest.

The processor 24 is a digital signal processor, a general processor, an application specific integrated circuit, field programmable gate array, control processor, digital circuitry, analog circuitry, combinations thereof or other now known or later developed device for implementing calculations, algorithms, programming or other functions. The processor 24 operates pursuant to instruction provided in the memory 18 or a different memory.

The processor 24 receives velocity estimates from the filter 20, velocity estimator 22, spatial filter 28, and/or scan converter 29. In one embodiment, motion estimates from the scan converter 29 are provided to the processor 24 to determine adaptations for the motion imaging.

In one embodiment, the processor 24 implements one or more of the algorithms, acts, steps, functions, methods or processes discussed herein with respect to FIGS. 1-7, either by processing the data and/or controlling operation of other components of the system 10. Different algorithms may be implemented, such as performing or controlling adjustment of clutter filtering as a function of spatial and/or temporal information, adjustment of thresholding as a function of spatial and/or temporal information, adjustment of spatial filtering as a function of spatial information, automatic steering for different regions, and/or region of interest expansion. Additional or multiple processors may be used to implement various aspects of the algorithms.

The instructions for implementing the processes, methods and/or techniques discussed above are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, filmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for adaptive motion imaging in medical diagnostic ultrasound, the method comprising:
   clutter filtering, thresholding, or combinations thereof first ultrasound information for a first location at a first time;
   adapting the clutter filtering, thresholding, or combinations thereof as a function of second ultrasound information for spatially, temporally, or spatially and temporally adjacent location, time, or location and time, respectively; and
   generating a velocity image as a function of data output from the adapted clutter filtering, thresholding or combinations thereof.

2. The method of claim 1 wherein clutter filtering, thresholding, or combinations thereof comprises at least clutter filtering, and wherein adapting comprises altering a rejection region, a rise time, or the rejection region and the rise time of the clutter filtering.

3. The method of claim 1 wherein clutter filtering, thresholding, or combinations thereof comprises at least thresholding, and wherein adapting comprises altering a threshold level.

4. The method of claim 1 wherein adapting comprises adapting as a function of the second ultrasound information for at least spatially adjacent location.

5. The method of claim 1 wherein adapting comprises adapting as a function of the second ultrasound information for at least temporally adjacent time.

6. The method of claim 1 wherein the first ultrasound information corresponds to a first velocity, and the second ultrasound information comprises a second velocity of the spatially adjacent location or temporally adjacent time, wherein adapting comprises (a) reducing a reject band of a clutter filter if the second velocity is lower than the first velocity and comprises (b) increasing the reject band and a threshold level if the second velocity is higher than the first velocity.

7. The method of claim 1 wherein the first ultrasound information corresponds to a first velocity; and
   further comprising adapting a spatial filter of the first velocity as a function of the second ultrasound information.

8. In a computer readable storage medium having stored therein data representing instructions executable by a programmed processor for adaptive motion imaging in medical diagnostic ultrasound, the storage medium comprising instructions for:
   clutter filtering first ultrasound information for a first location;

adapting the clutter filtering as a function of a velocity for spatially, temporally, or spatially and temporally adjacent location, time, or location and time, respectively; and generating a velocity image as a function of data output from the adapted clutter filtering.

9. The instructions of claim 8 wherein adapting comprises altering a pass-band of the clutter filtering.

10. A method for adaptive motion imaging in medical diagnostic ultrasound, the method comprising:

spatially filtering velocities for a first frame of data, the velocities representing different locations;

adapting the spatial filtering for a first velocity of the first frame of data, the adapting being as function of a second velocity of the first frame of data; and generating a velocity image as a function of an output of the spatially filtering.

11. The method of claim 10 wherein spatially filtering comprises filtering after velocity estimation and thresholding.

12. The method of claim 10 wherein adapting comprises modifying an extent of the spatial filtering as a function of a sign of the second velocity and an energy corresponding to the second velocity.

13. The method of claim 12 wherein modifying comprises reducing a length of a filter kernel if the sign is different than for other velocities in the filter kernel.

14. The method of claim 12 wherein modifying comprises decreasing the spatial filtering if the sign is different than for other velocities in a filter kernel and a threshold different in energy values of the filter kernel is satisfied.

15. A method for adaptive motion imaging in medical diagnostic ultrasound, the method comprising:

transmitting to each of a plurality of spatial locations from different angles;

estimating velocities for each of the spatial locations for each of the different angles;

identifying a maximum velocity of each of the spatial locations from the velocities of the different angles;

determining vessel orientations at the spatial locations; and setting steering angles for the spatial locations as a function of the vessel orientations and the maximum velocity.

16. The method of claim 15 wherein determining vessel orientations comprises identifying a largest velocity for each of the spatial locations from the velocities of the different angles and performing morphological processing with the largest velocities.

17. The method of claim 15 wherein identifying the maximum velocity comprises correcting aliasing.

18. The method of claim 15 wherein setting steering angles comprises identifying one of the different angles corresponding to the maximum velocity for each of the spatial locations, comparing the vessel orientation and the identified angle for each of the spatial locations, and setting the steering angles as a function of the comparison.

19. A method for adaptive motion imaging in medical diagnostic ultrasound, the method comprising:

receiving indication of a first region of interest for velocity;

setting a steering angle for the first region of interest as a function of a vessel orientation; and expanding the first region of interest to include a second region adjacent a first edge of the first region of interest, the second region of interest having scan lines with less steering angle than the steering angle of the first region of interest.

20. The method of claim 19 further comprising:

expanding the first region of interest to include a third region adjacent a second edge of the first region of interest opposite the first edge.

\* \* \* \* \*